United States Patent
Vrijer et al.

(10) Patent No.: US 6,776,772 B1
(45) Date of Patent: Aug. 17, 2004

(54) BALLOON CATHETER HAVING ELASTIC FILLING BODY FOR SUPPORTING A STENT

(75) Inventors: Rickie Bouma-de Vrijer, Roden (NL); Hugo Mulder, Winterswijk (NL)

(73) Assignee: Cordis Corporation, Miami Lakes, FL (US)

( * ) Notice: Subject to any disclaimer, the term of this patent is extended or adjusted under 35 U.S.C. 154(b) by 550 days.

(21) Appl. No.: 09/350,448

(22) Filed: Jul. 12, 1999

(30) Foreign Application Priority Data

Jul. 24, 1998 (NL) .............................................. 1009738

(51) Int. Cl.⁷ .............................................. A61M 29/00
(52) U.S. Cl. .................... 604/101.02; 604/103.07; 604/103.08; 606/194; 606/195; 623/1.11
(58) Field of Search .................... 604/96.01, 101.02, 604/101.01, 103.07, 103.08; 623/1.11, 1.12; 606/108, 109, 194, 195

(56) References Cited

U.S. PATENT DOCUMENTS 5,456,694 A * 10/1995 Marin et al. ............... 623/1.11
5,484,444 A * 1/1996 Braunschweiler et al. . 623/1.11
5,759,474 A   6/1998 Rupp
6,077,273 A * 6/2000 Euteneuer et al. .......... 606/108

FOREIGN PATENT DOCUMENTS

| EP | 0 553 960 A1 | 4/1993 |
| EP | 0 778 012 A2 | 11/1997 |
| WO | 96/38109 | 12/1996 |
| WO | 98/07390 | 2/1998 |

* cited by examiner

Primary Examiner—Brian L. Casler
Assistant Examiner—Jeremy Thissell
(74) Attorney, Agent, or Firm—Michael W. Montgomery

(57) ABSTRACT

The present invention relates to a balloon catheter for positioning a stent, including a tubular basic body with a proximal end and a distal end, and at least one lumen extending in between, a balloon close to the distal end which is connected to the lumen, and a stent crimped around the balloon, wherein a filling body of elastic material is arranged inside the balloon and has a size corresponding to at least the dimensions of the stent in compressed state, where the filling body is compressed by the stent in the compressed state.

4 Claims, 3 Drawing Sheets

BALLOON CATHETER HAVING ELASTIC FILLING BODY FOR SUPPORTING A STENT

BACKGROUND AND SUMMARY OF THE INVENTION

1. Technical Background

The present invention relates generally to medical devices, and more particularly to a stent delivery catheter system.

2. Discussion

Catheter systems are used in a variety of therapeutic applications, including many vascular treatments. Various types of catheters are available, such as balloon catheters for procedures such as angioplasty. Angioplasty can be used to treat vascular disease, in which blood vessels are partially or totally or partially blocked or narrowed by a lesion or stenosis. By way of example, the present invention will be described in relation to coronary and peripheral angioplasty and other vascular treatments. The coronary procedure is often referred to as PTCA, which stands for "percutaneous transluminal coronary angioplasty". However, it should be understood that the present invention relates to any stent delivery system having the features of the present invention, and is not limited to angioplasty.

The present invention relates to a balloon catheter for positioning a stent, having a tubular basic body with a proximal and a distal end. Close to the distal end a balloon has been affixed to the basic body which is connected with an inflation lumen extending through the basic body. A stent in a compressed shape has been arranged around the balloon member.

In operation, such a balloon catheter is generally loaded at the distal end with a stent crimped around the balloon member and introduced into a patient, and maneuvered to the site where the stent is to be positioned. By supplying via the inflation lumen a medium under pressure to the balloon, the balloon will expand and consequently the stent as well. After expanding the stent to the desired size, the pressure exerted by the medium is relieved, as a result of which the balloon will tend to shrink again and come loose of the expanded stent. Next, the catheter may be removed from the body, leaving the stent behind at the desired site.

When introducing the catheter it is obviously very important that the stent remains positioned on the balloon in a reliable manner, until the desired position has been reached. Accordingly, it is desirable to provide a balloon catheter that enhances position retention of a crimped stent, especially when the catheter is advanced or withdrawn in use.

A balloon catheter according to the invention is distinguished in that a filling body of elastic material is arranged inside the balloon. This elastic filling body has a size corresponding to at least the dimensions of the inner diameter of the stent in contracted state, where the filling body is compressed by the stent in its crimped state. As the crimped stent has been more or less clamped on the elastic filling body, a resistance is provided against movement by the stent in relation to the balloon. When crimping the stent around the balloon and the filling body, the filling body will be compressed to some extent. Because of its elasticity, a radial force is exerted continuously on the inside of the stent, causing constant friction and enhancing the position retention of the stent.

The elastic filling body may be tubular in shape, or may have a spiral shape and be made of a pliable material, such that the flexibility of the catheter may be enhanced.

In addition, the elastic filling body may be radiopaque, and thus visible on an imaging screen during fluoroscopy. The radiopaque filling body would thus render separate marker bands unnecessary.

Visibility of the stent on the imaging equipment in the catheterization laboratory may be enhanced by providing two filling bodies that are positioned at a distance from one another. The stent would be directly visible in the space between the two filling bodies.

The balloon catheter may have a basic body arranged with an outer tube and an inner tube. The inner tube is received inside the lumen of the outer tube, and the elastic filling body may be mounted on the inner tube. The filling body may be affixed to the inner tube in any suitable manner, including an adhesive, or by selecting the internal diameter of the filling body to be smaller than the outer diameter of the inner tube. The filling body is thereby clamped onto the inner tube. According to another suitable embodiment, the filling body and the inner tube are formed at the same time by coextrusion.

These and various other objects, advantages and features of the invention will become apparent from the following description and claims, when considered in conjunction with the appended drawings.

DETAILED DESCRIPTION OF THE PREFERRED EMBODIMENT

Figure 1:
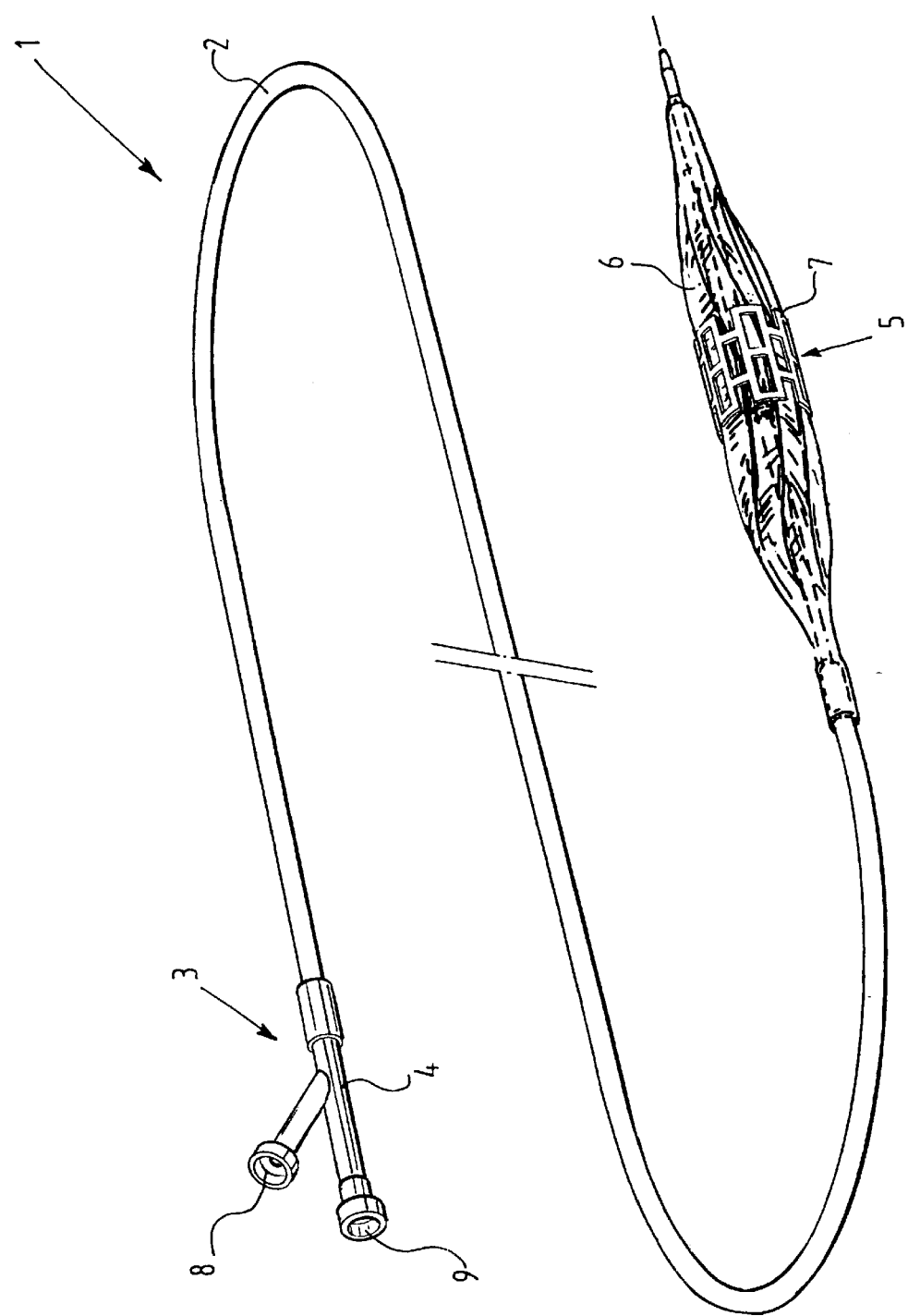
FIG. 1 is an external perspective view of a balloon catheter and stent delivery system, arranged according to the principles of the present invention.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a stent delivery system is depicted, with one of the preferred embodiments of the present invention being shown generally at 1.

The catheter 1 according to the present invention illustrated in FIG. 1 has a tubular basic body 2 with a proximal end 3 and a distal end 5. To the proximal end 3, a connecting member or hub 4 has been affixed, which has connections or ports 8 and 9 respectively. Ports 8 and 9 communicate with lumens 14 and 15 defined in the basic body 2.

Figure 2:
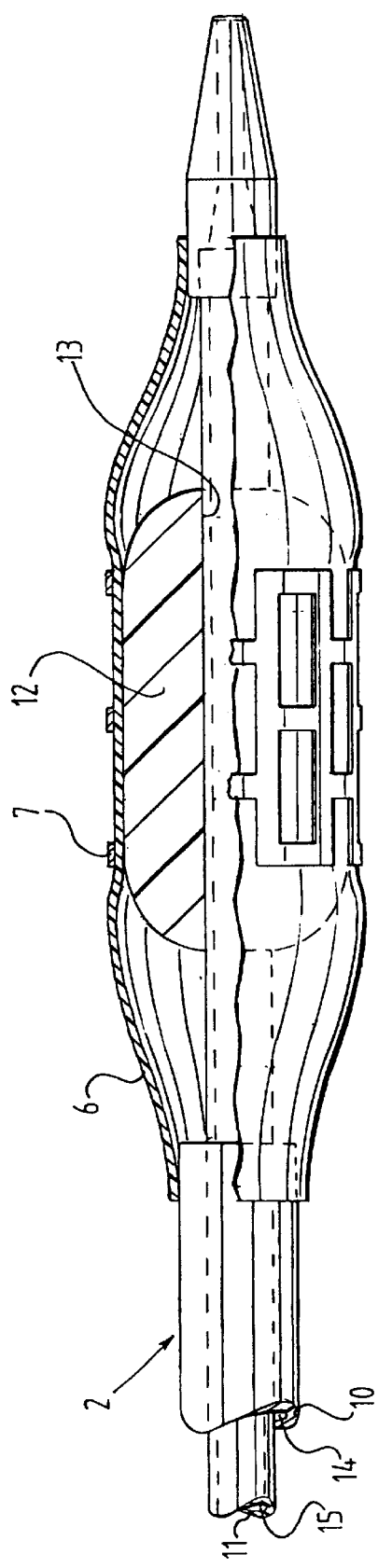
FIG. 2 is a partial longitudinal cross-section view of the catheter of FIG. 1.

At the distal end 5 of the catheter 1, a balloon 6 is arranged. A stent 7 has been crimped around the balloon 6. As can be seen in greater detail in FIG. 2, a filling body 12 has been received inside the balloon 6. In this embodiment, the filling body 12 is tubular in shape and has an internal diameter 13, which is somewhat smaller than the outer diameter of the inner tube 11 of the basic body 2. The filling body 12 is consequently clamped on to this inner tube 11. The basic body 2 in this preferred embodiment an outer tube 10 and an inner tube 11, leaving space for a lumen 14 in between, which is connected with the interior of the balloon 6.

Another lumen 15 has been arranged inside the inner tube 11, which for instance may be used for injecting contrast medium or receiving a guidewire. The lumens 14 and 15 are connected with the connections 8 and 9 of the connecting member 4 respectively, illustrated in FIG. 1.

The filling body 12 has preferably been made of an elastic material, so that when the stent 7 is clamped around the balloon 6 with the filling body 12 arranged inside, this filling body 12 is compressed elastically to some extent. Due to the elasticity, a constant perpendicular or normal force, and consequently a frictional force is exerted on the inside of the stent 7. The stent 7 is thus kept in position securely. In addition, the filling body 12 will protrude to some extent between the openings in the stent 7, contributing to additional fixation of the stent 7 on the balloon member.

When the stent 7 is to be positioned inside a patient, the distal end of the catheter 1 is introduced into the patient, and the catheter 1 is manipulated in such a way that its distal end will arrive up at the desired position.

Figure 3:
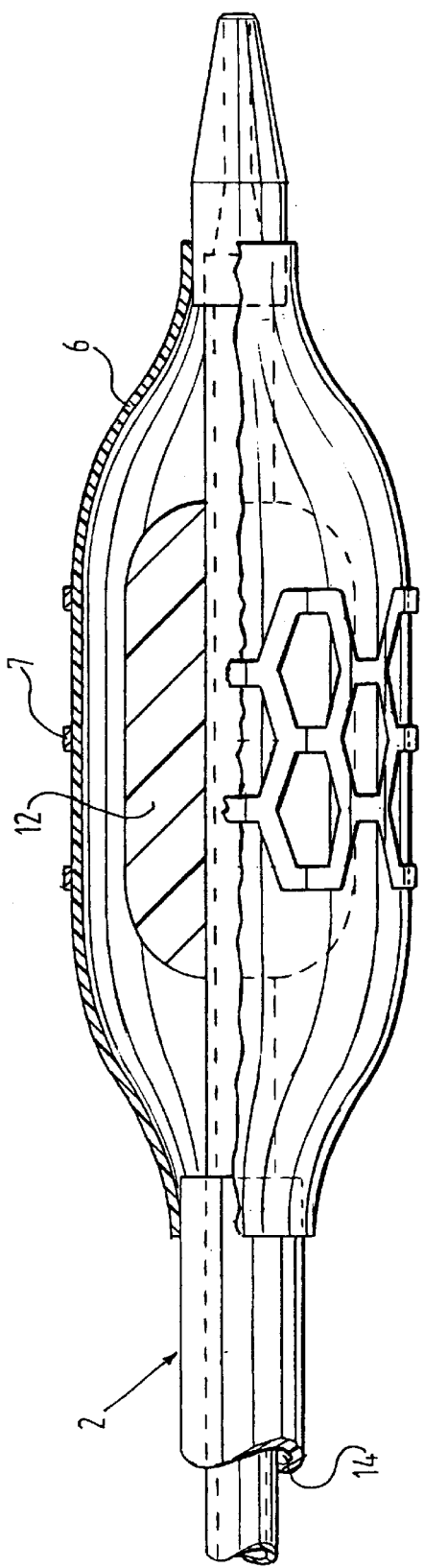
FIG. 3 is a partial longitudinal cross-section view of the catheter of FIG. 2, wherein the balloon is inflated.

As soon as the distal end, and in particular the stent 7, has reached the desired position, inflation medium is supplied under pressure, via the connection 8 and the lumen 14, to the inside of the balloon 6. As a result, the balloon 6 will expand to take on the shape illustrated in FIG. 3. At the same time, the stent 7 will be expanded to assume a larger diameter.

Inflation medium is supplied under sufficient pressure so that the stent 7 will obtain a required diameter, and will be positioned against the internal wall of a body vessel or a blood vessel so as to provide support.

Next, inflation medium may be removed from the balloon 6, as a result of which the balloon will tend to shrink and assume its original small diameter, and the catheter may be removed out of the patient's body. After removing the catheter, the stent 7 remains behind in the body vessel.

Figure 4:
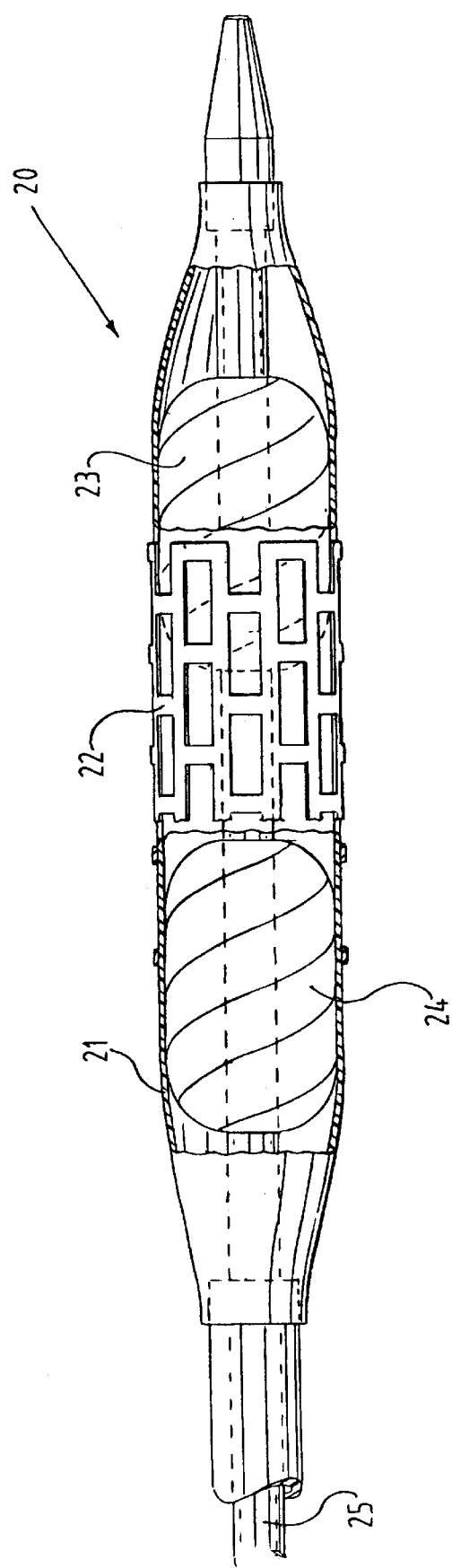
FIG. 4 is a partial longitudinal cross-section view of another embodiment of the present invention.

With the catheter 20 as illustrated in FIG. 4, two filling bodies 23, 24 have been received in the balloon 21. These filling bodies 23, 24 are positioned at a distance from one another, and both support one end of the stent 22 crimped around the balloon. The filling bodies 23, 24 are spiral shaped, and clamp elastically on the inner tube 25. In addition, the filling bodies 23, 24 can properly follow the curves of the inner tube 25.

The filling bodies 23 and 24 may be preferably made of a radiopaque material, so that they can be visualized properly when using fluoroscopy in a catheterization laboratory. The catheter according to the invention consequently does not require separate marking bands.

As the filling bodies 23, 24 have been arranged at a distance from one another, the stent 22 remains properly visible in the space in between the filling bodies 23, 24 on a fluoroscope. If one continuous filling body would be employed, the stent might become invisible while it is being positioned.

The filling body or the filling bodies as employed with the catheter according to the invention may be given different embodiments. Besides the coil shape illustrated in the Figures, whether or not forming a spiral, a filling body may also comprise protruding edges in between which the stent will be placed in contracted state.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A stent delivery system with a balloon catheter for positioning a stent, comprising:

a tubular shaft with a proximal end and a distal end, and at least one lumen extending in between, an inelastic balloon near the distal end of the shaft which is connected with the lumen, a stent crimped around the balloon; and a filling body of elastic and radiopaque material arranged inside the balloon and affixed to the shaft, the filling body having a size corresponding to at least a dimension of the stent in a compressed state, where the filling body is compressed by the stent when the stent is in a compressed state.

2. The stent delivery system with a balloon catheter as set forth in claim 1, wherein the filling body has a spiral shape.

3. The stent delivery system with a balloon catheter as set forth in claim 1, wherein an inner tube has been arranged inside the lumen of the basic body, and the filling body has been secured to the inner tube.

4. A balloon catheter and stent for treating a patient, comprising:

a tubular shaft with a proximal end and a distal end, and at least one lumen extending in between;

an inelastic balloon affixed near the distal end of the shaft which is connected to the lumen; and a filling body of elastic and radiopaque material arranged inside the balloon and affixed to the shaft; wherein the filling body is sized to have an outer profile that is greater than a deflated and pleated inner profile of the balloon, and less than an inflated inner profile of the balloon;

wherein the filling body is adapted to be elastically compressed by a stent crimped about the balloon.

* * * * *